(12) United States Patent
Emslie et al.

(10) Patent No.: US 9,848,896 B2
(45) Date of Patent: Dec. 26, 2017

(54) FEMORAL SIZING JIG, FEMUR RESECTING SYSTEM, AND METHOD

(71) Applicant: CORIN LIMITED, Gloucestershire (GB)

(72) Inventors: Ian James Emslie, Gloucestershire (GB); Johan Bellemans, Langdorp (BE); Jan Maria Karel Victor, Bruges (BE)

(73) Assignee: CORIN LIMITED, Gloucestershire (GB)

( * ) Notice: Subject to any disclaimer, the term of this patent is extended or adjusted under 35 U.S.C. 154(b) by 754 days.

(21) Appl. No.: 14/353,026

(22) PCT Filed: Oct. 19, 2012

(86) PCT No.: PCT/GB2012/052608
§ 371 (c)(1),
(2) Date: Apr. 20, 2014

(87) PCT Pub. No.: WO2013/057514
PCT Pub. Date: Apr. 25, 2013

(65) Prior Publication Data
US 2014/0336659 A1 Nov. 13, 2014

(30) Foreign Application Priority Data

Oct. 21, 2011 (GB) .................................. 1118219.3

(51) Int. Cl.
*A61B 17/58* (2006.01)
*A61B 17/17* (2006.01)
(Continued)

(52) U.S. Cl.
CPC ........ *A61B 17/1764* (2013.01); *A61B 17/155* (2013.01); *A61F 2/4657* (2013.01); *A61F 2/38* (2013.01); *A61F 2002/4668* (2013.01)

(58) Field of Classification Search
CPC .................. A61B 17/15; A61B 17/151; A61B 17/154–17/155; A61B 17/17; A61B 17/1764
(Continued)

(56) References Cited

U.S. PATENT DOCUMENTS 5,423,827 A 6/1995 Mumme et al.
5,776,137 A 7/1998 Katz
(Continued)

FOREIGN PATENT DOCUMENTS

DE 102010013258 A1 6/2011
EP 2277460 A1 1/2011
(Continued)

OTHER PUBLICATIONS

International Search Report of PCT Patent Application No. PCT/GB2012/052608 dated Dec. 14, 2012.
(Continued)

*Primary Examiner* — Tatiana Nobrega
*Assistant Examiner* — Jessica Weiss

(57) ABSTRACT

A femoral sizing jig for use in total arthroplasty of left and right knees, comprises a femoral body, an external-rotation-angle arm which is, preferably pivotable, relative to the femoral body for setting an external angular rotation of a left or right femur, at least one of a cutting-jig guide and a cutting jig which is, preferably slidable, relative to the femoral body and in unison with movement of the external rotation-angle arm, and a medial posterior-condylar locator which is movable in unison with the movement of the external-rotation-angle arm, so as to maintain a fixed or substantially fixed relative distance with a medial side of the at least one of a cutting-jig guide and a cutting jig. A posterior-referencing femur resecting system using said femoral sizing jig and a method of resecting a femur at a
(Continued)

knee joint relative to the medial posterior condyle are also provided.

18 Claims, 6 Drawing Sheets

(51) Int. Cl.
    *A61B 17/15*     (2006.01)
    *A61F 2/46*     (2006.01)
    *A61F 2/38*     (2006.01)

(58) Field of Classification Search
    USPC .............................. 606/87–90, 96–98, 104
    See application file for complete search history.

(56) References Cited

U.S. PATENT DOCUMENTS

| | | | |
|---|---|---|---|
| 6,013,081 A | 1/2000 | Burkinshaw et al. | |
| 6,258,095 B1* | 7/2001 | Lombardo | A61B 17/154 606/87 |
| 6,458,135 B1* | 10/2002 | Harwin | A61B 17/155 606/88 |
| 7,488,324 B1* | 2/2009 | Metzger | A61B 17/155 33/511 |
| 8,591,516 B2* | 11/2013 | Metzger | A61B 17/157 606/86 R |
| 2007/0173851 A1* | 7/2007 | McMillen | A61B 17/1764 606/87 |
| 2011/0046685 A1 | 2/2011 | Faure et al. | |

FOREIGN PATENT DOCUMENTS

| | | |
|---|---|---|
| JP | 2001525536 A | 12/2001 |
| JP | 2011078529 A | 4/2011 |

OTHER PUBLICATIONS

Search Report of British Patent Application No. GB1118219.3 dated Jan. 27, 2012.

Office Action of counterpart Japanese Patent Application No. 2014536334 dated Sep. 27, 2016.

\* cited by examiner

FEMORAL SIZING JIG, FEMUR RESECTING SYSTEM, AND METHOD

The present invention relates to a femoral sizing jig for use in total arthroplasty of left and right knees, a femur resecting system using the said femoral sizing jig, and to a method of resecting a femur at a knee joint using the medial posterior condyle as a datum.

Total knee replacement (TKR) surgery is a common orthopaedic procedure conducted to reduce joint pain and restore mobility, particularly in arthritic patients. Relative to patient satisfaction after total hip replacement surgery, knee functionality is in general not as satisfactory and patient outcome scores are reported as poor in many cases. A suggestion is that knee kinematics maybe improved by a better understanding of relationship of joint-line preservation and co-lateral isometry.

One common surgical approach is the conventional 'measured resection' technique in TKR that aims to restore the original surface geometry of the knee. It is common within such measured resection systems to size the knee and set external rotation via a centrally pivoting sizing guide which may be connected to an intramedullary rod extending longitudinally within the femur from the distal end. However, as arthritic knees are often deformed by cartilage or bone wear, dysplasia or ligament attrition and contracture, this technique can result in ligament imbalance and instability as the restoration of joint line is altered by the degree of external rotation of the femoral component chosen by the surgeon.

Another technique is a 'ligament balancing' technique where the surgeon aims to restore balance in the soft tissue structures of the knee post TKR by the position of bony cuts used to set the position of the femur. An instrument known as a tensioner is used with a central pivot point that relies on a tibio-femoral separation (set by the ligament length) to determine the position of the femoral component. In using a central pivot point, resection depth relative to the posterior femoral condyle is variable and often therefore results in a different centre of rotation of the femur after surgery compared to the natural pre-operated knee during flexion. This will further thus affect ligament isometry and can lead to instability at different flexion angles.

The present invention discloses a new method and instrumentation for a 'ligament balancing' technique and setting of external rotation for conventional TKR techniques.

The described instrument aims to blend both measured resection and ligament balancing techniques by providing tibio-femoral dependant positioning in combination with a measured resection about the centre of the medial femoral condyle in the sagittal plane.

As the medial side of the femur is the generally less worn, more stable and congruent side of the knee, TKR performed with this technique will produce more normal postoperative kinematics by ensuring that knee flexion is restored after surgery.

A novel aspect of the present invention is the provision of an instrument which allows tibio-femoral separation, tensioning both medial and lateral collateral ligaments, whilst allowing rotation about the medial condyle of the knee. The concept will maintain the resection depth of the medial condyle at a constant value, independent of external rotation value, therefore maintaining the pre-operative rotation of the knee joint.

A further aspect of the invention is the provision of shims to locate on the posterior feet of the instrument in cases where there is severe wear of the posterior femoral condyles to ensure preservation of the natural joint line.

The invention seeks to provide a solution to these problems.

According to a first aspect of the invention, there is provided a femoral sizing jig for use in total arthroplasty of left and right knees, the jig comprising a femoral body, an external-rotation-angle arm which is movable relative to the femoral body for setting an external angular rotation of a left or right femur, at least one of a cutting-jig guide and a cutting jig which is movable relative to the femoral body and in unison with movement of the external-rotation-angle arm, and a medial posterior-condylar locator which is movable in unison with movement of the external-rotation-angle arm, so as to maintain a fixed or substantially fixed relative distance with a medial side of the at least one of a cutting-jig guide and a cutting jig.

According to a second aspect of the invention, there is provided a posterior-referencing femur resecting system comprising a varus valgus alignment guide, a distal femoral resection jig, a femoral sizing jig in accordance with the first aspect of the invention, and a multi-plane femoral resection jig for posterior femoral resection, anterior femoral resection, posterior chamfer cutting and anterior chamfer cutting.

According to a third aspect of the invention, there is provided a method of resecting a femur at a knee joint relative to the medial posterior condyle, the method comprising the steps of: a] setting a femoral external rotation angle relative to a medial posterior condyle by pivoting an external-rotation-angle arm of a femoral sizing jig; b] applying a femoral sizing jig to a distal face of the femur, whereby the medial posterior condyle is directly or indirectly seated on a posterior-condylar locator; and c] using a cutting-jig guide and/or cutting jig to facilitate resection of a femoral face of the femur relative to the medial posterior condyle.

The present invention will now be more particularly described, by way of example only, with reference to the accompanying drawings, in which.

Figure 1:
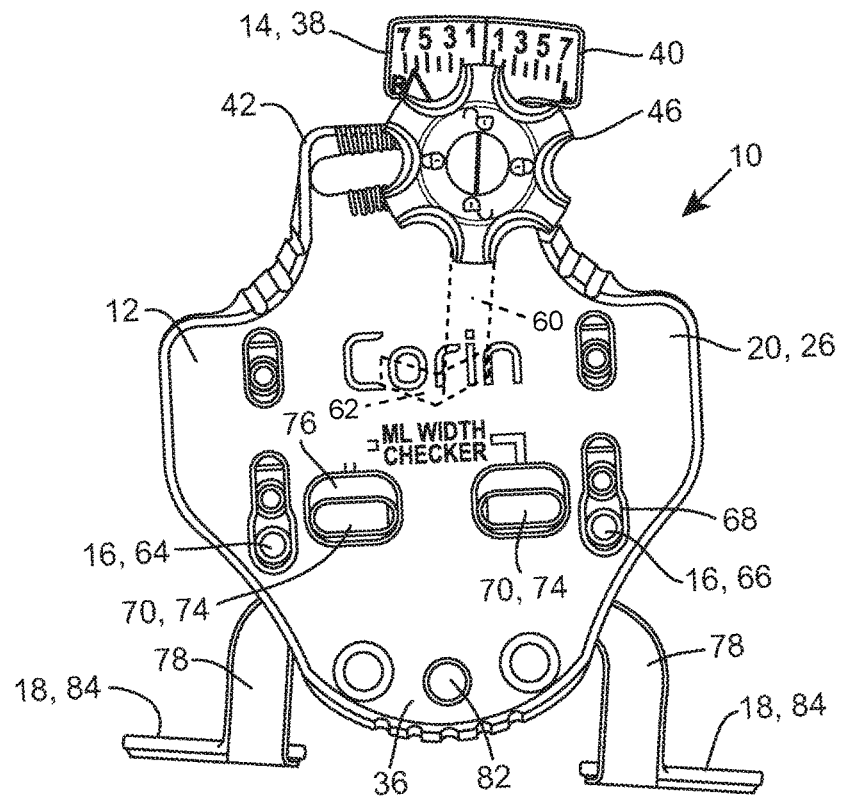
FIG. 1 shows a front side view of one embodiment of a femoral sizing jig, in accordance with the first aspect of the invention.

Referring to the drawings, there is shown one embodiment of a femoral sizing jig 10, preferably formed of a suitable surgical material such as stainless steel or titanium, which comprises a femoral body 12, an external-rotation-angle arm 14, a cutting-jig location guide 16 and a posterior-condylar locator 18. The femoral body 12 in this case is a generally flat housing 20 dimensioned to be compatible with a distal end 22 of a femur 24. The housing 20 comprises preferably flat front and rear major walls 26, 28 and minor side walls 30 which all together define an interior cavity 32.

The external-rotation-angle arm 14 in this case is elongate having a substantially uniform lateral extent along at least a majority of its longitudinal extent. The arm 14 is pivotably mounted within the interior cavity 32 at or adjacent to its lower end 34 and at or adjacent to the lower end 36 of the housing 20. The arm 14 is a close fit to at least one major wall 26, 28 within the housing 20 such that the interior surface of the front and/or rear major walls 26, 28 act as supporting and guiding surfaces.

A rotational-angle scale 38 is fixedly provided at the upper end 40 of the arm 14, exterior of the housing 20 and adjacent to the upper end 42 thereof. An indicator 44 is preferably provided on the upper end 42 of the housing 20, which in this case is a pointer, and indicates a rotational angle on the scale 38.

A locking device 46 is provided on the femoral body 12 to hold the external-rotation angle arm 14 in a set position relative to the femoral body 12. In this case, the locking device 46 extends through a slot 48 in the upper portion of the femoral body 12. A plurality of femoral-body teeth 50 is provided adjacent to the slot 48, in parallel or substantially parallel with each longitudinal edge of the slot 48 on the front major wall 26. A locking tooth 52 is provided on a preferably spring-biased knob or grip 54 which passes through the lateral extent of the slot 48. The knob or grip 54 is preferably spring biased towards the slot 48 so that the locking tooth 52 tends towards an engaged condition. However, the locking knob or grip 54 can also be axially rotated so that the locking tooth 52 aligns with the longitudinal extent of the slot 48. This allows free sliding movement of the knob or grip 54 over the femoral-body teeth 50. Once an angular rotation of the femur 24 is decided, the knob or grip 54 is pulled outwards and turned, and the spring force is then allowed to draw the locking tooth 52 into engagement between the femoral-body teeth 50.

Also provided within the housing 20 is the cutting-jig location guide 16. This may conveniently include a rigid plate body 55 which is linearly slidable within the cavity 32, guided by a plurality of spaced apart guide pins 56 engaging in respective guide slots 58 formed in the front and rear major walls 26, 28 of the femoral body 12. Additionally, it is preferred that the external-rotation-angle arm 14 extends through the location-guide body 55, and is slidable generally side-to-side therein.

The location guide 16 is connected to the external-rotation-angle arm 14 so that the two elements are movable in unison. To provide for this interengagement, a pin and guide channel 60, 62 are provided on the arm 14 and the location-guide body 55, respectively.

The pin 60 is provided partway along the longitudinal extent of the arm 14, and the guide channel 62 is provided symmetrically about the vertical central axis of the location guide 16. However, the location of the pin 60 and the guide channel 62 could conceivably be reversed.

The guide channel 62 includes an angled longitudinal extent, in this case defining a V15 shape pointing towards the lower end 36 of the housing 20. The guide channel 62 preferably comprises two rectilinear channel portions which intersect at or substantially at the longitudinal line of symmetry of the femoral body 12. The guide channel 62 is also open along both longitudinal sides, defining an open sided slot for receiving the pin 60. However, the distal longitudinal side remote from the arm 14 may be closed, if necessary.

The pin 60 is thus slidable in the guide channel 62 as the arm 14 is pivoted, whereby the location guide 16 is urged upwardly or downwardly in the in use housing 20.

The guide channel 62 may be arcuate rather than straight sided.

The location guide 16 also includes lateral and medial locator elements 64, 66. In this case, the locator elements 64, 66 are apertures through the location-guide body 55. The apertures are preferably cylindrical, and thereby provide a surgical drill guide. To enable access to the locator elements 64, 66, the front and rear major walls 26, 28 of the femoral body 12 include elongate slots 68 aligned with the path of movement of the apertures 66, 68.

Beneficially, the location guide 16 also includes a width-checker connector 70 for releasably connecting a femoral width-checker device 72. See FIG. 5e. In this case, the width-checker connector 70 includes two laterally spaced apart openings 74 adjacent to a lower edge of the location-guide body 55. Two further elongate slots 76 are again included in the front major wall 26 of the femoral body 12, and these are aligned with the path of movement of the openings 74 so that the femoral width-checker device 72 can slide relative to the femoral body 12 whilst remaining engaged in the openings 74 of the location-guide body 55.

The posterior-condylar locator 18 is in this case integrally formed as one piece with the external-rotation-angle arm 14. The posterior-condylar locator 18 comprises two legs 78 which extend at least substantially coplanar from a lower end portion 80 of the arm 14, but above the pivot point 82, and laterally from the femoral body 12. A foot 84 extends at or substantially at right angles to the plane of the legs 78 and from a distal end thereof.

Each foot 84 preferably includes a substantially planar plate, tab, tongue or platform 86 for location on the posterior of the medial condyle. As such, the posterior-condylar locator 18 is pivotable in unison with the arm 14, and also relative to the femoral body 12. The said platform 86 may be angled relative to the plane of longitudinal symmetry of the femoral body 12, so as to project away therefrom. This enables the femoral body 12 to be as small and compact as possible whilst still allowing location of the foot 84 on the posterior medial condyle.

Figure 2:
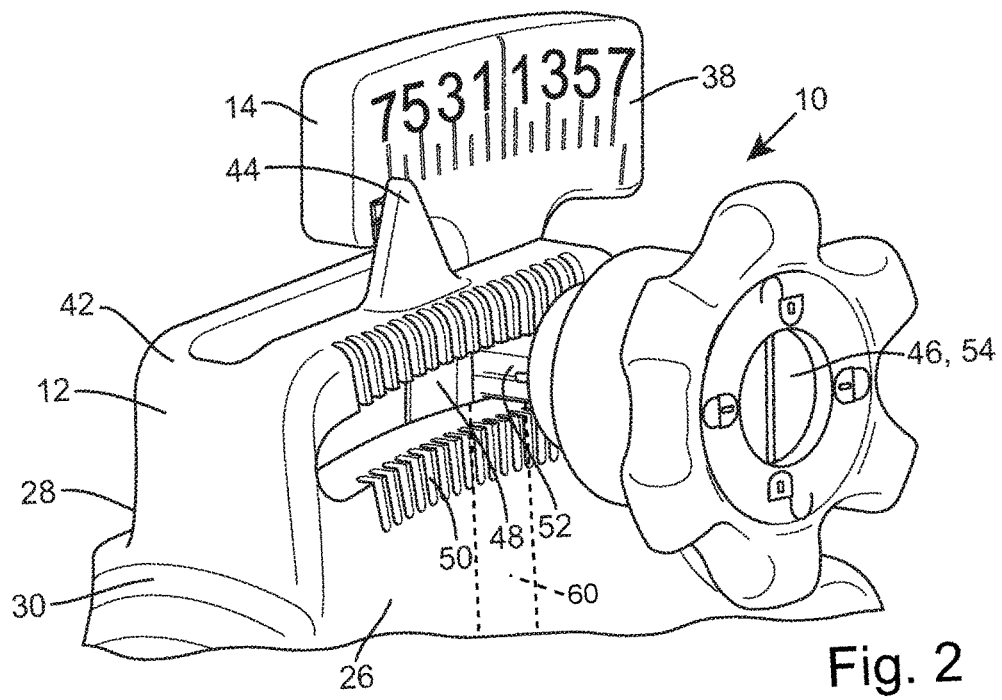
FIG. 2 shows an enlarged perspective view of a top portion of the femoral sizing jig, showing a scale and locking element.
Figure 3:
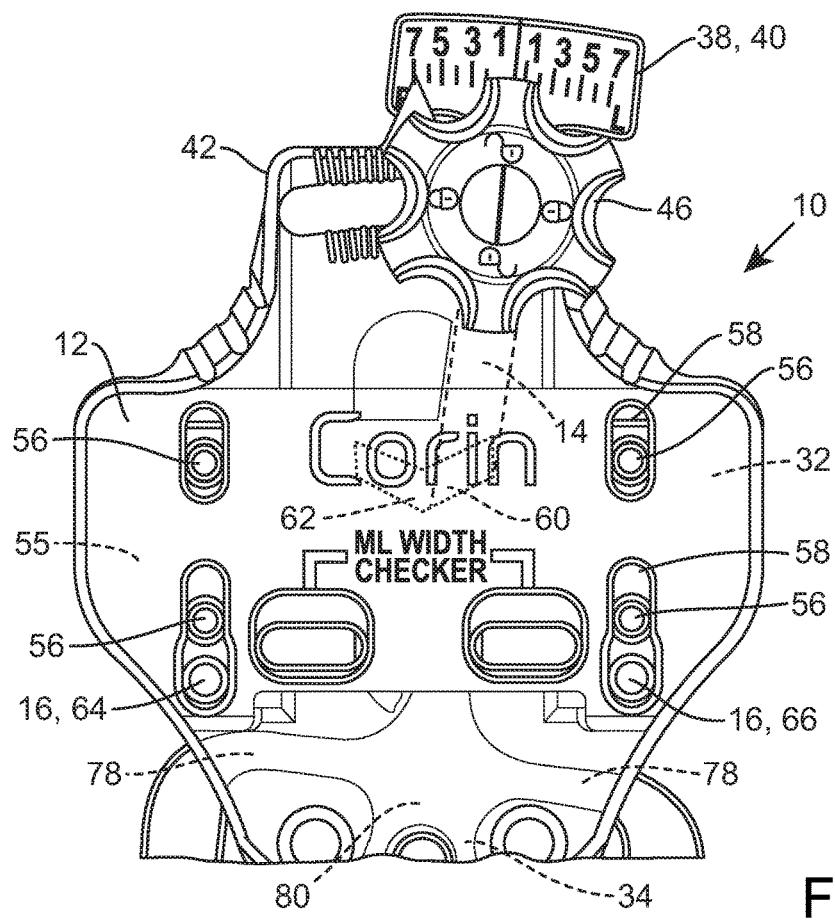
FIG. 3 shows an enlarged view in partial phantom showing the internal components of the femoral sizing jig.
Figure 4:
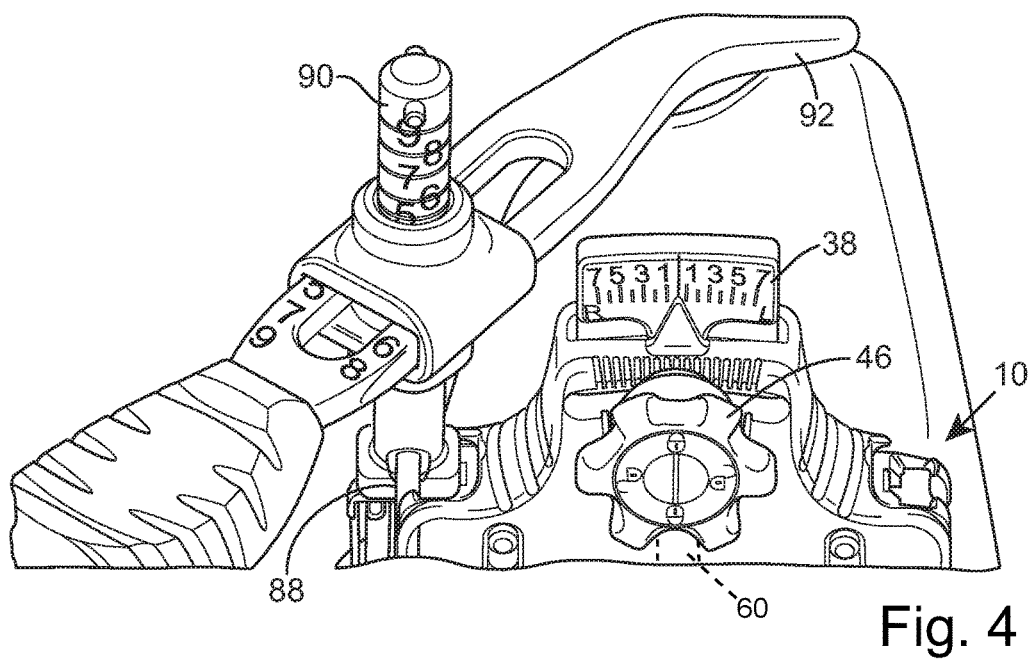
FIG. 4 shows an enlarged of a top portion of the femoral sizing jig, including a stylus post and stylus.

The location guide 16 also advantageously includes a stylus-holder connector 88 for receiving a stylus holder 90. In this case, the stylus holder 90 is a post, as shown in FIG. 2, and the stylus 92 is attached thereto. The post and/or stylus 92 may include gradations and/or measurements for use during sizing.

The stylus holder 90 is a releasable push-fit into the connector 88, formed as an opening formed in a side of the location-guide body 55, and as such the femoral body 12 is open to allow the stylus holder 90 to project unhindered therefrom. Since the stylus holder 90 is connectable to the location-guide body 55, it is movable in unison with the location guide body 55 and thus also the arm 14.

Referring now to FIGS. 5a to 5h, the use of the femoral sizing jig 10 as part of posterior-referencing femur resecting system will now be described. In general surgery, the proximal end 94 of the tibia 96 has already been prepared and resected to take a tibial plate of the prosthesis. However, the tibia can be prepared after the femoral bone cuts. The tibial preparation generally takes into account neutral varus/valgus alignment and the resection typically includes a 3 degree posterior (or other) slope.

A distal end 22 of the femur 24 is then prepared by using an intramedullary canal drill 98 to penetrate the cortex. The drill bit is inserted into the medullary canal, medial to the mid-point between the lateral and medial condyles 100, 102, and approximately 10 mm anterior to the origin of the posterior cruciate ligament.

Figure 5A:
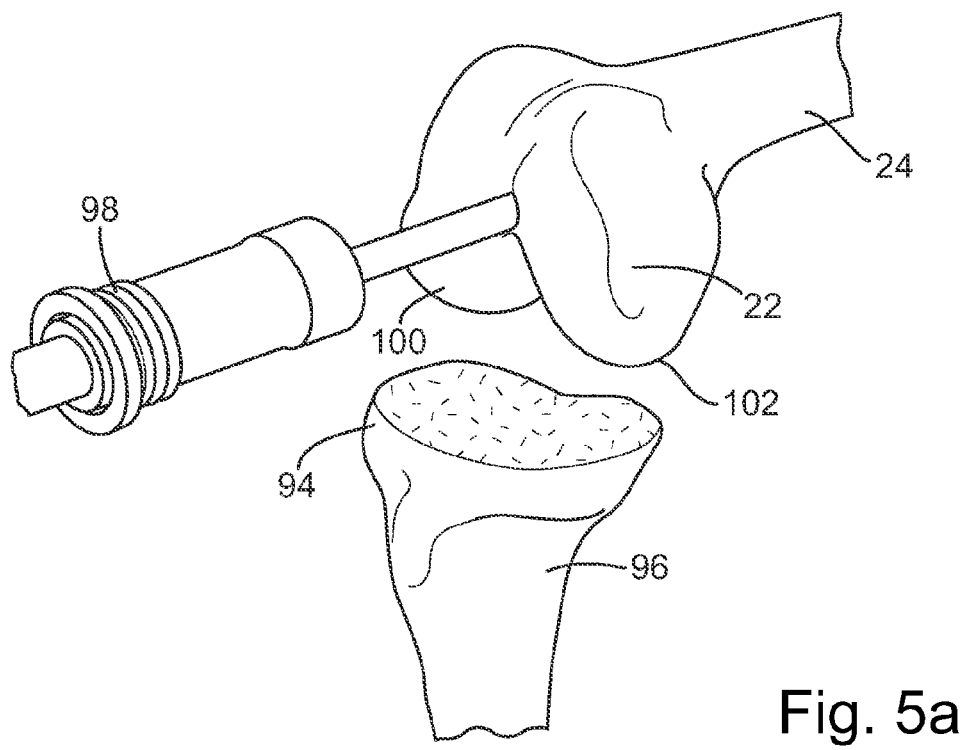
FIGS. 5a to 5h show a method of resecting a femur at a knee joint relative to the medial posterior condyle, using the femoral sizing jig.
Figure 5B:
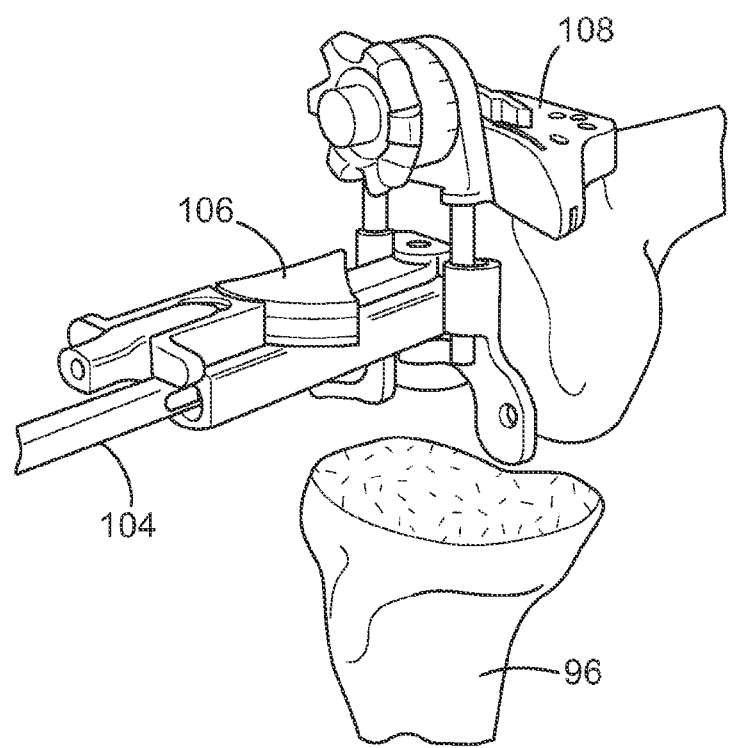
Figure 5C:
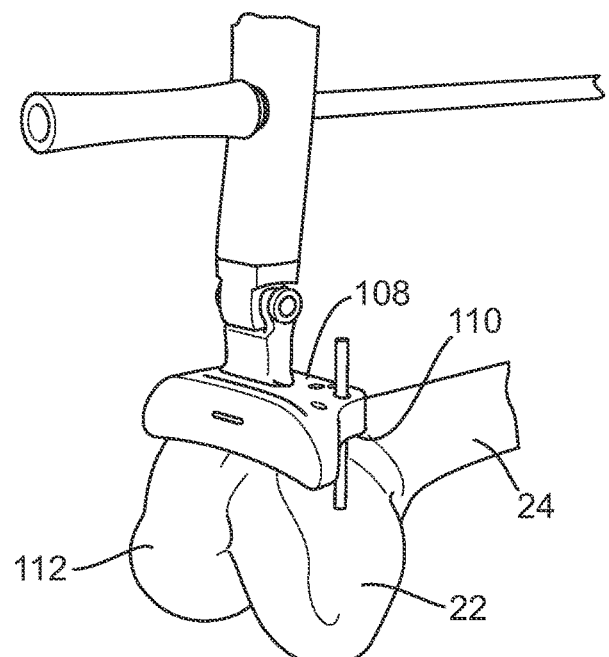
Figure 5D:
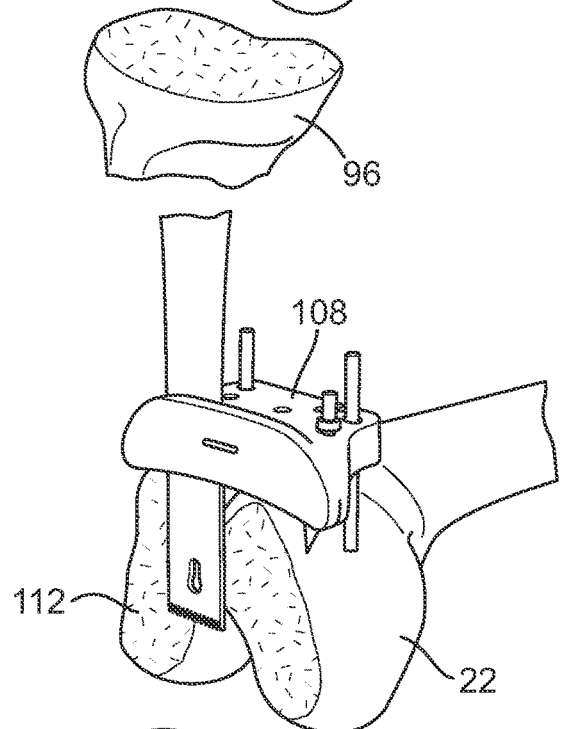
Figure 5E:
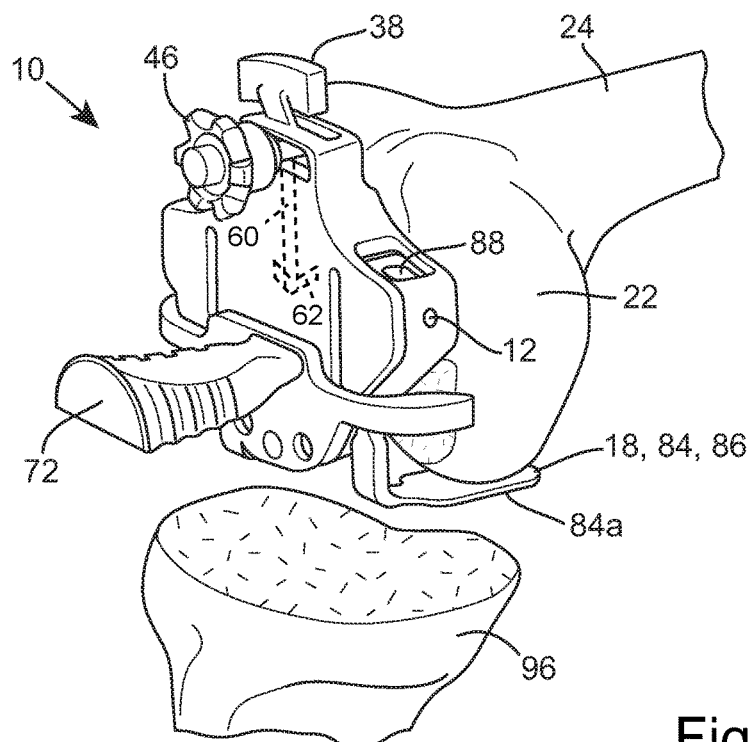
Figure 5F:
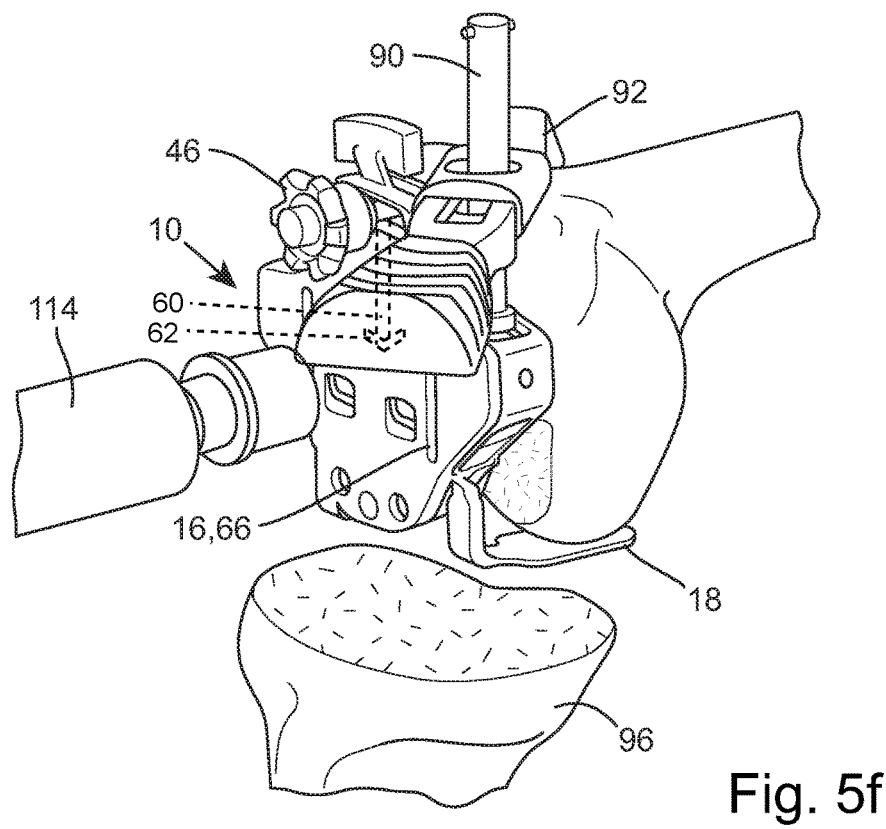
Figure 5G:
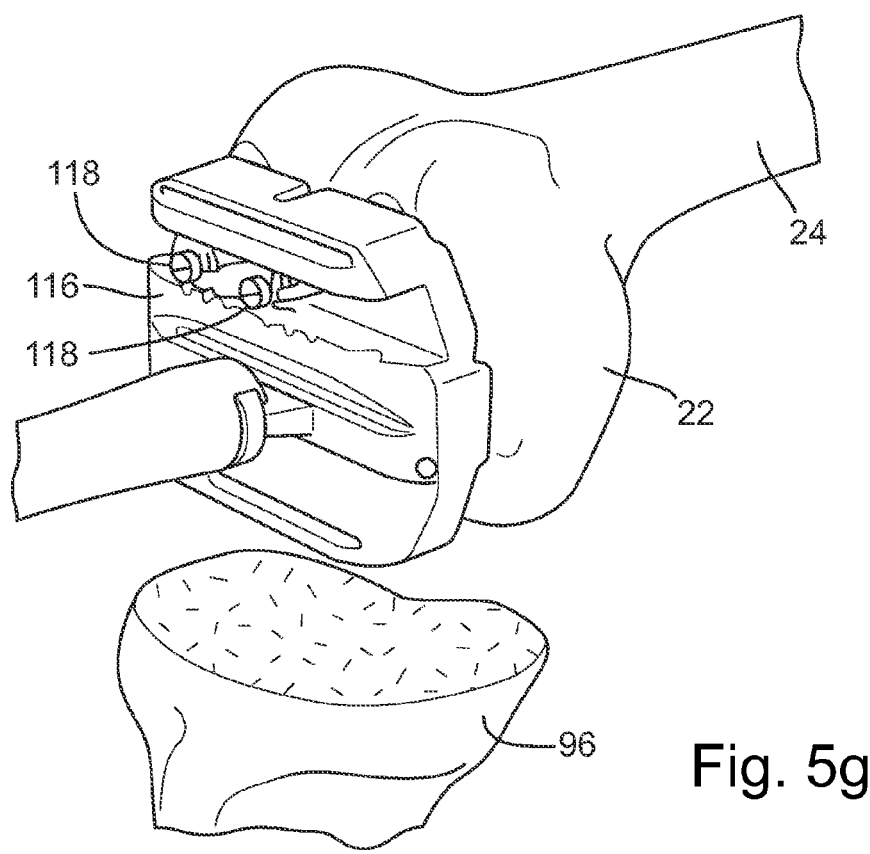
Figure 5H:
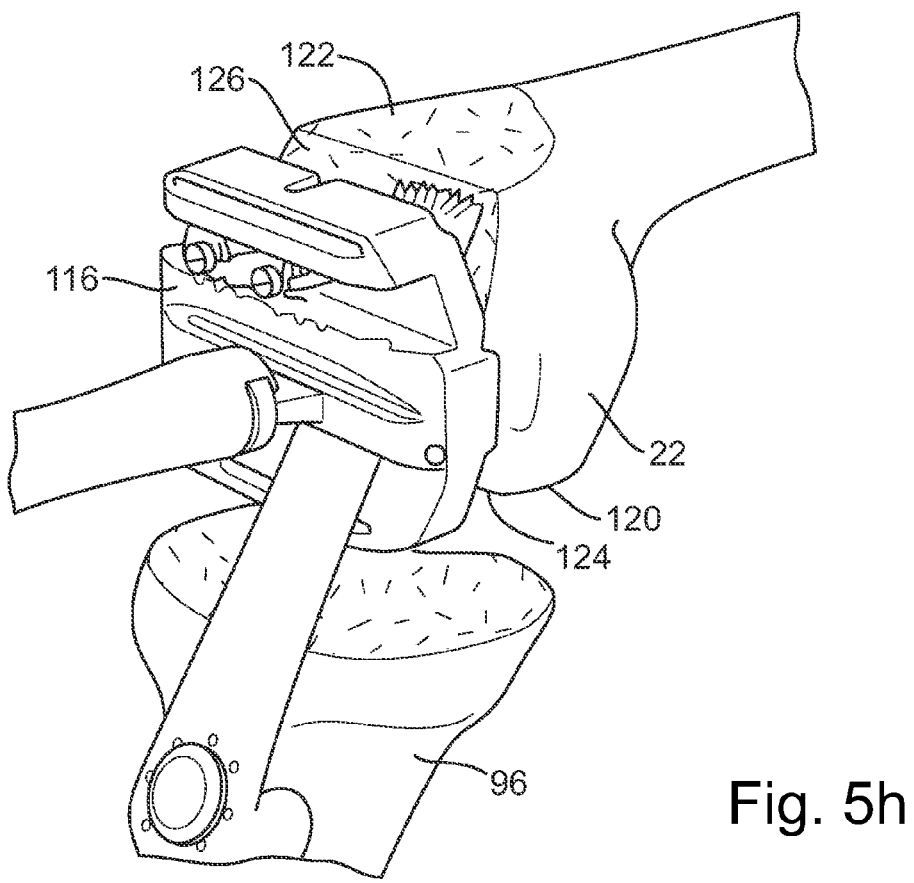

An intramedullary rod 104 is then inserted and varus/valgus alignment along with distal face resection depth is set via a femoral distal alignment jig 106 located on the intramedullary rod 104. A femoral resection jig 108 is located on the anterior cortex 110 of the distal end 22 of the femur 24 via the femoral distal alignment jig 106, and is then pinned in place at the selected proximal/distal position to suit the amount of bone desired to be removed. With the intramedullary rod 104 and femoral distal alignment jig 106 removed, a first resection across the distal face 112 of the femur 24 is conducted, as shown in FIG. 5d.

The external-rotation-angle arm 14 of the femoral sizing jig 10 is then set to its required offset angle, and locked in place using the above-described locking device 46. This offset angle causes effective counter-rotation of the femoral body 12, and therefore also of the cutting-jig location guide 16, relative to the medial-side foot 84 of the posterior condylar locator 18, due to the medial-side foot 84a and the medial-side locator element 66 having a fixed spatial relationship. In other words, as the arm 14 is moved angularly, the location-guide body 55 moves upwardly or downwardly within the femoral body 12.

The medial-side foot 84 therefore moves in unison with the medial-side locator element 66 through the location-guide body 55, maintaining the separation therebetween, but imparting effective rotation of the femoral body 12 and thus also of the lateral-side locator element 64.

With the femoral sizing jig 10 then located on the resected distal face 112, both rotational alignment and femoral sizing in conjunction with the femoral stylus 92 is possible. The femoral sizing jig 10 is a posterior referencer allowing for, in this case, 9 mm of bone resection from the medial posterior femoral condyles 102 at all angular settings of the femoral sizing jig 10.

The medial-side foot 84 is located on the medial posterior femoral condyle 102, and the rear major wall 28 positioned against the resected distal face 112. The femoral width checker device 72 can be attached to the openings 74 in the location-guide body 55 to confirm rotational alignment of the femoral component and to conduct a secondary medial/lateral sizing check once the anterior/posterior size is confirmed.

With the stylus 92 connected to the stylus holder 90, and the stylus holder 90 engaged with the medial and/or lateral stylus-holder connectors 88, an optimal femoral size is determined. A surgical drill 114 is then used to form two peg holes in the resected distal face 112 utilising the positioned lateral and medial locator elements 64, 66. See FIG. 5f.

With the femoral sizing jig 10 removed, a multi-plane femoral resection jig 116 is positioned onto the resected distal face 112 and held in position with locator pins 118 which are inserted into the medial and lateral pin holes formed using the femoral sizing jig 10. Further pins can also be used to hold the multi-plane femoral resection jig 116 more firmly to the resected distal face 112, if necessary.

Posterior femoral resection 120 and anterior femoral resection 122 are undertaken, and a posterior chamfer 124 and an anterior chamfer 126 are now formed, all being guided by the multi-plane femoral resection jig 116. See FIG. 5h.

Following these steps, an initial femoral trial is undertaken. Balancing of the flexion and extension gaps is performed, rotational adjustment is restored, final tibial and femoral preparation is undertaken, and patella resection, sizing and trial is implemented. Trial reduction in flexion and extension is then performed, and finally insertion of the definitive components of the prosthesis is undertaken.

Since the medial posterior condyle forms the datum for external rotation angle of the femur, it is feasible that the distal end face does not need to be resected initially.

Furthermore, it is possible that the medial locator element could be dispensed with, if any further cutting jig includes a reference element based on the medial posterior condyle. For example, this could be similar to the foot of the posterior-condylar locator of the femoral sizing jig.

Although the external-rotation-angle arm of the femoral sizing jig is set to its required offset angle, and locked in place using the locking device to achieve the predetermined offset angle, the locking device may be unlocked allowing the external-rotation-angle arm to initially freely move. In this case, with the femoral sizing jig applied to the distal end of the femur, the offset angle can be intra-operatively set to achieve optimum ligament balancing between flexion and extension checking of the knee. Once the ligament balance has been decided, the locking device can be locked.

It may also be advantageous to utilise one or more shims on or adjacent to the or each posterior-condylar locator. A shim is beneficial in reconstructing the patient's natural joint line which may be necessary if the posterior condyles of the femur are worn. A plurality of shims of different thicknesses is typically provided for appropriate selection therefrom. The or each shim may be mountable via mounting means on one or both posterior-condylar locators.

Additionally or alternatively, the femoral sizing jig could include one or more cutting jig guides and/or a cutting jig. For example, it would be feasible to include at least an anterior and/or posterior femoral resection cutting jig or guide in the femoral sizing jig to establish a rotational setting relative to the medial condyle. This may be in the form of a slot extending laterally across the top and/or bottom portion of the femoral body to allow for an initial anterior and/or posterior femoral resection, instead of forming medial and lateral pin holes, as described above. Additionally or alternatively, anterior and/or posterior chamfer cuts could be performed that would establish the rotational setting relative to the medial condyle.

It is thus possible to provide a femoral sizing jig which, as part of at least a posterior 30 referencing femur resecting system, ensures maintenance of a natural joint line of a patient's leg and facilitates co-lateral isometry post total knee replacement. It is intended that the use of the femoral sizing jig of the present invention during total knee arthroplasty places the prosthetic components in an anatomical position with respect to the physiological axis of the knee joint, whilst maintaining stability throughout the full range of knee flexion. The femoral sizing jig provides for setting of external rotation when using standard or conventional total knee replacement techniques. The femoral sizing jig facilitates measured resection and ligament balancing techniques following femoral dependant positioning utilising a datum taken from the medial posterior femoral condyle. As the medial side of the femur is the more stable compartment of the knee, total knee replacement performed with this technique will product more normal postoperative kinematics by ensuring that knee flexion is restored. The femoral sizing jig of the present invention is additionally highly advantageous in that it provides for a single jig being used in total arthroplasty of both left and right knees.

The embodiments described above are provided by way of examples only, and various other modifications will be apparent to persons skilled in the art without departing from the scope of the invention as defined by the appended claims.

The invention claimed is:

1. A femoral sizing jig for use in total arthroplasty of left and right knees, the jig comprising a femoral body, an external-rotation-angle arm which is movable relative to the femoral body and which sets an external angular rotation of a left or right femur, at least one of a cutting-jig guide and a cutting jig which is movable relative to the femoral body and in unison with movement of the external rotation-angle arm when setting the external angular rotation of the left or right femur, wherein the cutting-jig guide is slidable within the femoral body, the cutting-jig guide and the external-rotation-angle arm being interengaged by a pin and guide channel, the guide channel having an angled V-shaped longitudinal extent with two linear portions forming the V-shaped longitudinal extent, and a medial posterior-condylar locator which is movable in unison with movement of the external-rotation-angle arm and pivotable relative to the femoral body when setting the external angular rotation of the left or right femur, so as to maintain a fixed or substantially fixed relative distance between the medial posterior-condylar locator and a medial side of the at least one of the cutting-jig guide and the cutting jig.

2. The femoral sizing jig as claimed in claim 1, wherein the external-rotation-angle arm is pivotable within the femoral body.

3. The femoral sizing jig as claimed in claim 1, wherein the external rotation-angle arm includes a scale which indicates a femoral external rotation angle.

4. The femoral sizing jig as claimed in claim 3, further comprising a locking element which locks the external-rotation-angle arm relative to the femoral body.

5. The femoral sizing jig as claimed in claim 4, wherein the locking element includes a plurality of femoral-body teeth on the femoral body, and at least one locking tooth on a locking knob which is engagable between the femoral-body teeth.

6. The femoral sizing jig as claimed in claim 1, wherein the medial posterior-condylar locator extends laterally from a lower portion of the femoral body.

7. The femoral sizing jig as claimed in claim 1, wherein the cutting-jig guide includes a lateral condyle drill guide which is adapted to be rotated by the movement of the external-rotation-angle arm, due to the fixed or substantially fixed relative distance between the medial side of the cutting-jig guide and the medial posterior-condylar locator.

8. The femoral sizing jig as claimed in claim 1, wherein the cutting jig includes at least one cutting aperture configured to allow at least one of posterior femoral resection, anterior femoral resection, posterior chamfer cutting and anterior chamfer cutting to be made, the cutting jig and the medial posterior-condylar locator being movable in unison such that the medial posterior-condylar locator and the cutting aperture are movable in unison with a fixed relative distance therebetween.

9. The femoral sizing jig as claimed in claim 1, further comprising a stylus-holder connector at or adjacent to at least one side of the femoral body.

10. The femoral sizing jig as claimed in claim 1, further comprising a width-checker connector formed as part of the cutting-jig guide and/or the cutting jig.

11. The femoral sizing jig as claimed in claim 1, further comprising at least one shim located on or adjacent to the medial posterior-condylar locator to assist with ligament balancing.

12. A posterior-referencing femur resecting system comprising a varus valgus alignment guide, a distal femoral resection jig, a femoral sizing jig as claimed in claim 1, and a multi-plane femoral resection jig for posterior femoral resection, anterior femoral resection, posterior chamfer cutting and anterior chamfer cutting.

13. A method of resecting a femur at a knee joint relative to the medial posterior condyle, the method comprising the steps of: a] setting a femoral external rotation angle relative to the medial posterior condyle by pivoting the external rotation-angle arm of the femoral sizing jig as claimed in claim 1; b] applying the femoral sizing jig to the distal face of the femur, whereby the medial posterior condyle is directly or indirectly seated on the medial posterior-condylar locator; and c] using the cutting-jig guide and/or cutting jig to facilitate resection of the femoral face of the femur relative to the medial posterior condyle.

14. The method as claimed in claim 13, wherein, in step b], the medial posterior-condylar locator includes a shim on which the medial posterior condyle is seated.

15. The method as claimed in claim 13, wherein, in step c], the cutting-jig guide is utilized to provide at least one locator on a lateral condyle of the distal face of the femur.

16. The method as claimed in claim 13, wherein, in step c], the cutting-jig guide is utilized to provide a further locator on the medial condyle.

17. The method as claimed in claim 13, further comprising a step e] prior to step a] of making a first resection across a distal face of a femur, and in step b] applying the femoral sizing jig to the first resection.

18. The method as claimed in claim 15, further comprising a step d], wherein at least one femoral resection jig is utilized located on the femur via the at least one locator to form a posterior femoral resection, anterior femoral resection, a posterior chamfer and/or an anterior chamfer cut.

* * * * *